US012811008B2

(12) United States Patent
Noël et al.

(10) Patent No.: US 12,811,008 B2
(45) Date of Patent: Nov. 24, 2026

(54) METHOD OF USING DIGITAL TWIN BIOMARKER PROFILES FOR IMPROVED SPORTS TRAINING AND PERFORMANCE, WELLNESS AND HEALTHCARE OUTCOMES

(71) Applicant: Ai-Genetika Inc., Quebec (CA)

(72) Inventors: Louis-Philippe Noël, Quebec (CA); Carl Hémond, Levis (CA); William John Redmond, Quebec (CA); Stephanie Kamgnia Wonkap, Saint-Hubert (CA); Manon Fradin, Quebec (CA); Mildred Zulay Delgado, Quebec (CA)

(73) Assignee: BioTwin Holding International Inc. (CA)

(*) Notice: Subject to any disclaimer, the term of this patent is extended or adjusted under 35 U.S.C. 154(b) by 523 days.

(21) Appl. No.: 17/655,024

(22) Filed: Mar. 16, 2022

(65) Prior Publication Data

US 2022/0301715 A1 Sep. 22, 2022

Related U.S. Application Data

(60) Provisional application No. 63/162,258, filed on Mar. 17, 2021.

(51) Int. Cl.
*G16H 50/20* (2018.01)
*G01N 33/68* (2006.01)
(Continued)

(52) U.S. Cl.
CPC ......... *G16H 50/20* (2018.01); *G01N 33/6893* (2013.01); *G16H 20/30* (2018.01); *G16H 50/30* (2018.01)

(58) Field of Classification Search
CPC ........ G16H 50/20; G16H 20/30; G16H 50/30; G16H 10/40; G16H 15/00; G16H 20/60; G16H 50/50; G16H 50/70; G01N 33/6893
See application file for complete search history.

(56) References Cited

U.S. PATENT DOCUMENTS

| | | | | |
|---|---|---|---|---|
| 7,867,511 | B2 * | 1/2011 | Anderson | A62D 3/33 514/622 |
| 10,210,307 | B2 * | 2/2019 | Huang | A61B 5/150022 |
| 10,340,030 | B2 * | 7/2019 | Bagaev | G16H 10/20 |
| 2008/0274474 | A1 * | 11/2008 | Krul | C12Q 1/00 435/7.1 |
| 2009/0307181 | A1 * | 12/2009 | Colby | G16B 20/10 706/54 |
| 2012/0165703 | A1 * | 6/2012 | Bottum | G16H 20/30 600/595 |

(Continued)

OTHER PUBLICATIONS

Corral-Acero J, Margara F, Marciniak M, Rodero C, Loncaric F, Feng Y, Gilbert A, Fernandes JF, Bukhari HA, Wajdan A, Martinez MV, Santos MS, Shamohammdi M, Luo H, Westphal P, Leeson P, DiAchille P, Gurev V, Mayr M, Geris L, Pathmanathan P, Morrison T, Cornelussen R, Prinzen F, Delhaas T, oltra A, Sitg (Year: 2020).*

(Continued)

*Primary Examiner* — Sun M Li
(74) *Attorney, Agent, or Firm* — Matthew W. Mitchell; Mitchell Law PLLC

(57) ABSTRACT

Provided herein is a method of using digital twin biomarker profiles for improved sporting, therapy, wellness and healthcare outcomes by comparing digital twin biomarker profiles at discrete interval to discern and evaluate data progression. Also provided is a sampling kit for collecting human fluid samples for analysis and generation of digital twin data.

18 Claims, 5 Drawing Sheets

(51) Int. Cl.
*G16H 20/30* (2018.01)
*G16H 50/30* (2018.01)

(56) References Cited

U.S. PATENT DOCUMENTS

| | | | | |
|---|---|---|---|---|
| 2013/0209985 | A1 | 8/2013 | Hoke et al. | |
| 2018/0030538 | A1* | 2/2018 | Redei | G01N 33/6893 |
| 2019/0005200 | A1* | 1/2019 | Zimmerman | G16H 50/30 |
| 2020/0131581 | A1* | 4/2020 | Jain | G16H 50/20 |
| 2021/0005324 | A1* | 1/2021 | Bostic | G16H 50/20 |
| 2021/0050089 | A1* | 2/2021 | Mohammed | A61B 5/0205 |
| 2021/0196175 | A1* | 7/2021 | Levy | A61B 5/02055 |
| 2021/0202107 | A1* | 7/2021 | Bostic | G16H 20/10 |
| 2021/0212629 | A1* | 7/2021 | Li | A61B 5/0263 |

OTHER PUBLICATIONS

Ahmed Z, Mohamed K, Zeeshan S, Dong X. Artificial intelligence with multi-functional machine learning platform development for better healthcare and precision medicine. Database (Oxford). Jan. 1, 2020;2020:baaa010. doi: 10.1093/database/baaa010. PMID: 32185396; PMCID: PMC7078068. (Year: 2020).*

Vitali F, Li Q, Schissler AG, Berghout J, Kenost C, Lussier YA. Developing a 'personalome' for precision medicine: emerging methods that compute interpretable effect sizes from single-subject transcriptomes. Brief Bioinform. May 21, 2019;20(3):789-805. doi: 0.1093/bib/bbx149. PMID: 29272327; PMCID: PMC (Year: 2019).*

Laubenbacher et al., " Using digital twins in viral infection: Personalized computer simulations of infection could allow more effective treatments", Science; Mar. 12, 2021; 371(6534): pp. 1105-1106.

Croatti et al.. , "On the Integration of Agents and Digital Twins in Healthcare", Journal of Medical Systems 44,161 (2020), pp. 1-8.

Bjornsson et al., "Digital twins to personalize medicine", Genome Medicine 12, 4 (2020), pp. 1-4.

Fagherazzi., "Deep Digital Phenotyping and Digital Twins for Precision Health: Time to Dig Deeper", Journal of Medical Internet Research, 2020, vol. 22, Issue 3, e16770, pp. 1-4.

* cited by examiner

METHOD OF USING DIGITAL TWIN BIOMARKER PROFILES FOR IMPROVED SPORTS TRAINING AND PERFORMANCE, WELLNESS AND HEALTHCARE OUTCOMES

CROSS REFERENCE TO RELATED APPLICATION

The present application claims priority to U.S. Provisional Patent Application Ser. No. 63/162,258 filed on Mar. 17, 2021, the entirety of which is incorporated herein by reference.

FIELD OF THE INVENTION

The invention relates to the fields of digital twins and artificial intelligence. The expression "digital twin" refers to digital data representation of a physical object, machine or living organisms such as animals or human beings. This invention more particularly relates to the use of digital twins and artificial intelligence for animal and human beings in order to provide on-going monitoring, analysis, prediction and personalized recommendations for sports training, wellness and healthcare.

BACKGROUND OF THE INVENTION

A "digital twin" in the context of a living organism such as a human being is a collection of digital information indicative of health or other health-related parameters like age, fitness, body mass index, history of disease, genetics, etc. It is a digital model based on real-world measurements (known as artifacts) that provides a dynamic representation over time of the physiological status of a subject. Each human being can be provided with a digital twin comprising a modest or large amount of data on various biomarkers such as levels of various enzymes, hormones, minerals, etc. There are about 115,000 known human metabolites that have been identified and over 1.5M that are estimated and non identified. Along with over 25K proteins and various genetic markers, they represent the "biomarkers". Biomarkers can be proteins, fats, nutrients, waste products, hormones, gene variants, and various levels of detectable species or metabolites present in the body, in secretions or excretions.

The use of "multi-omics" profiling technologies (genomics, proteomics, metabolomics, epigenomic etc.) has exploded in recent years and begun to advance understanding of disease and reactions to lifestyles, nutrition, genetics, exercise and environment.

Concurrently, artificial intelligence is known to be used to simulate outcomes and to compare data sets with known data sets in order to draw conclusions based on previous knowledge and ongoing knowledge acquisition (machine learning acquisition). For example, in the healthcare sector, detection of high levels of cholesterol in blood can be a predictor of the risk of eventual atherosclerosis and heart disease. Artificial intelligence would predict that abnormally rising blood cholesterol levels are a predictor of heart disease. Furthermore, genetics, diets and exercise levels are also known to modulate blood cholesterol. Such correlations are known and studied for a number of diseases or conditions. As such, it is known to use artificial intelligence to provide risk assessment and recommendations based on specific test data collected on patients.

However, so far, the use of digital twins and artificial intelligence has been limited. For example, a device commercialized under the brand Lumen™ is a small Bluetooth-connected device similar in shape to a vape pen where users exhale. The device measures $CO_2$ levels. The $CO_2$ level indicates if the user's metabolism being in fat burning mode or carbohydrate burning mode. A fat-burning mode is said to be directly related to a lower level of $CO_2$, and also to weight loss: The device also comes with a specific smartphone application which provides diet recommendations and scores based on the $CO_2$ reading. This is directed towards athletes or the weight-loss industry. Of note, the apparatus and method only focus on one parameter, namely $CO_2$, and as such does not create a digital twin.

Another known service is provided by "Let's get Checked". It provides the kind of home testing that is traditionally provided by health care establishments. Thus, it is a home testing kit mailed to clients who have selected one or more tests to be performed. Fluid samples (such as blood or urine) are directly collected by the user/client. After self-collection, samples are mailed back to a lab for analysis, process and medical check. Up to 50 biomarkers can be measured in total within various tests. The biomarkers include hormones, cholesterol, bacteria counts, etc. The company reports to clients their results with emphasis on abnormal results and findings of infection. They also recommend repeated testing over time to track important biomarkers variations such as cholesterol levels. However, the reports provide readings of individual biomarkers without providing profiles of combined biomarkers.

On the genetic side, companies such as "23andMe™" provide home kits mailed to clients who collect saliva samples and mail back the kit for genetic testing. A laboratory analyzes saliva sample to determine the genotype and variant identification and reports every genetic anomalies that may be statistically linked to certain diseases. Because gene expression and diseases can also be modulated by environmental factors and lifestyle, the results are not fully predictive of outcome and doesn't reflect the phenotype. Indeed, genetic sequencing does not take into account other biomarkers, especially the ones that may change over time nor profiles of multiple biomarkers.

The "MolecularYou™" service provides detailed reports based on blood tests. These reports use various biomarkers present in blood and rely on a combination of genotyping and traditional biomarker measurements. Clients receive a report which summarizes a high level snapshot of disease risks and recommendations. This report includes, an organ health assessment, risk of contracting specific diseases, inflammation score, medications that may pose a risk, and individual test results compared with optimal ranges. Arivale offered a similar service until it was closed in 2019.

The iCarbonX service is collecting a large amount of biomarker data such as DNA, RNA, proteins, microbiomes, etc. and is using artificial intelligence to develop correlations between theses biomarkers and specific disease state. ICarbonX then issues recommendations based on these findings.

The Onegevity service provides biometric data measurements, artificial intelligence, and personalized wellness recommendations. The service allows for home sample collection of microbiomes, blood and saliva which are mail back to a lab for results and recommendations to improve health and wellness.

Other services of blood contents measurement analysis include for example: Nightingale and Thriva combine blood analysis technology, identify disease risks and make comparisons with ideal ranges of blood components.

The above described services do not feature a holistic phenotype profiling of a digital twin so as to provide more accurate predictions and recommendations. A full digital twin representation over time provides a full phenotype of a subject.

The integration of digital twins in healthcare has also been discussed by Croatti et al. in *Journal of Medical Systems* 44:161 (2020) in an article entitled *On the Integration of Agents and Digital Twins in Healthcare*. The article discussed the context of strategic planning by creating a digital twin of a hospital and running simulations on the digital replica to provide more effective care interventions. Meanwhile, Bjornsson, B., et al, discussed the use of genotyping to provide personalized medicine in *Digital twins to personalize medicine, Genome Medicine* 12:4 (2020).

In *Deep Digital Phenotyping and Digital Twins for Precision Health: Time to Dig Deeper*, (*J Med Internet Res* 2020; 22 (3): e16770) Fagherazzi, emphasizes the growing importance of digital twin for providing precision medicine and personalized therapeutic strategy. The article stresses the known desideratum of personalized medicine but does not provide a complete method and system as presented herein.

Thus, despite recent advancements and desired progress in this area, there remains a need for novel and improved methods for generating a personalized and more complete digital twin to effectively monitor, analyse, assess, predict parameters and outcomes that are useful in sports training, wellness or healthcare settings and precision medicine.

There is also a need for developing improved artificial intelligence directed to the same purposes. Also, there is a need for supporting professionals involved in sports training or injury rehabilitation, wellness and medicine by providing ready access to biomarker data and artificial intelligence to predict and improve patient or client outcomes.

The present invention addresses these needs and other needs as it will be apparent from the review of the disclosure and description of the features of the invention hereinafter.

BRIEF SUMMARY

In a general sense, the present technology provides a method of using digital twin biomarker profiles for improved sporting, therapy, wellness and healthcare outcomes comprising of:

a) sampling a plurality of biomarkers from a subject by at least one method of sample collection;
b) analysing and measuring said biomarkers to create a digital twin based on the human actual phenotype;
c) comparing the digital twin phenotyping to known values (reference);
d) reporting results of the comparison performed in step c);
e) optionally repeating steps a) to d) at discrete time intervals;
f) generating a set of recommended actions or patterns response to the results reported in the step d);
g) optionally generating simulations or predictions based on the results of step d) and/or the recommendations of step f).

Also provided is method in accordance with the above, where the biomarkers are indicative of parameters useful to benchmark sports performance.

Also provided is a method in accordance with the above, where the biomarkers are indicative parameters and values or comparators of wellness, of therapy results, or of health or disease or progression thereof.

In the methods above, the biomarkers number at least 10, preferably at least 100 and more preferably at least 200.

Also provided is a novel sampling kit for implementing step a) in accordance with claim 1, the sampling kit comprising of biofluid sample collection device and instructions for use.

Additional aspects, advantages and features of the present invention will become more apparent upon reading of the following non-restrictive description of preferred embodiments which are exemplary and should not be interpreted as limiting the scope of the invention.

BRIEF DESCRIPTION OF THE FIGURES

In order for the invention to be readily understood, embodiments of the invention are illustrated by way of example in the accompanying figures.

Figure 1:
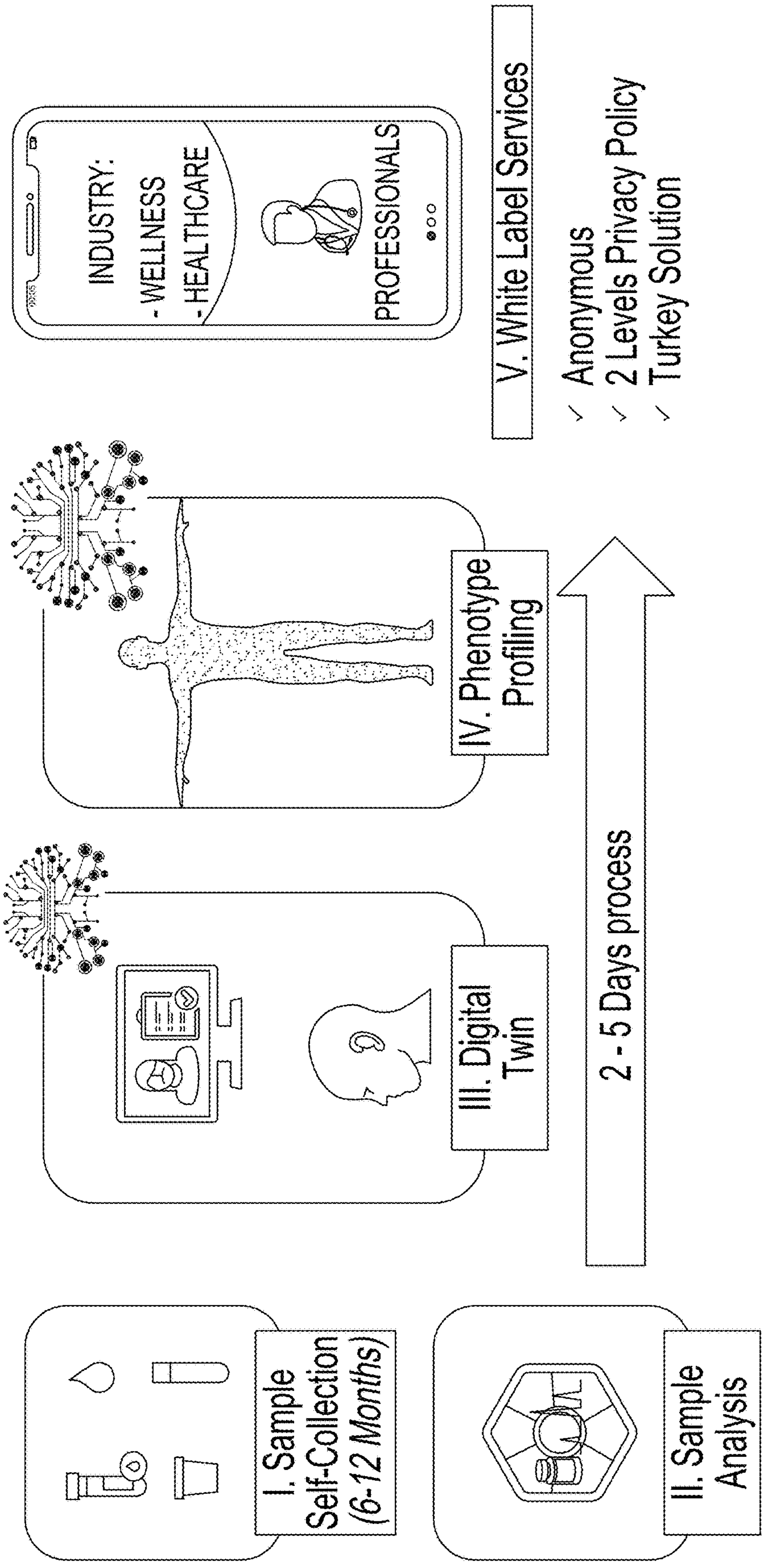
FIG. 1 is a flow chart of the system and sequence in accordance with one particular embodiment of the invention.

Further details of the invention and its advantages will be apparent from the detailed description included below.

DETAILED DESCRIPTION OF EMBODIMENTS

In the following description of the embodiments, references to the accompanying figures are illustrations of one or more examples by which the invention may be practiced. It will be understood that other embodiments may be made without departing from the scope of the invention disclosed. Unless defined otherwise, all technical and scientific terms used herein have the same meaning as commonly understood by one of ordinary skill in the art to which the invention belongs.

In a most general sense, the invention provides a system and method to effectively detect and predict physiological conditions, outcomes and variations in sports training, wellness and healthcare and precision medicine. The invention also provides means of detecting, and in some instances preventing, the appearance/disappearance, proliferation or manifestations of diseases conditions in live beings.

When used herein, the term «biomarker» is meant to refer to useful measurements from tissue or fluid samples linked to a specific phenotype. It includes excretions or secretions from a live being, including, without being exhaustive, levels of minerals, hormones, proteins, fats, sugars, vitamins, metabolites, microbiomes, analytes, enzymes, antigens and antibodies and including various molecular markers and cells. Biomarkers can also include gene variants, alleles and other genetic information. Biomarkers can also include species such as telomeres and their length measurements.

When used herein, the term "wellness" is meant to be general and refer for example to overall health, sleep, nutrition, life expectancy, biological age, energy levels, body mass index or other similar measurements, flexibility, strength and other similar features.

The term "sport" is meant to be general and refer to competitive and non-competitive sports or other physical activities.

The term "health" is meant to be general and refer to all parameters and biomarkers indicative of health or disease states or progression thereof.

In the context of the present specification, a "server" is a computer program that is running on appropriate hardware and is capable of receiving requests (e.g., from electronic devices) over a network (e.g., a communication network), and carrying out those requests, or causing those requests to be carried out. The hardware may be one physical computer or one physical computer system, but neither is required to be the case with respect to the present technology. In the present context, the use of the expression a "server" is not intended to mean that every task (e.g., received instructions or requests) or any particular task will have been received, carried out, or caused to be carried out, by the same server (i.e., the same software and/or hardware); it is intended to mean that any number of software elements or hardware devices may be involved in receiving/sending, carrying out or causing to be carried out any task or request, or the consequences of any task or request; and all of this software and hardware may be one server or multiple servers, both of which are included within the expressions "at least one server" and "a server".

In the context of the present specification, "electronic device" is any computing apparatus or computer hardware that is capable of running software appropriate to the relevant task at hand. Thus, some (non-limiting) examples of electronic devices include general purpose personal computers (desktops, laptops, netbooks, etc.), mobile computing devices, smartphones, and tablets, and network equipment such as routers, switches, and gateways. It should be noted that an electronic device in the present context is not precluded from acting as a server to other electronic devices. The use of the expression "an electronic device" does not preclude multiple electronic devices being used in receiving/sending, carrying out or causing to be carried out any task or request, or the consequences of any task or request, or steps of any method described herein. In the context of the present specification, a "client device" refers to any of a range of end-user client electronic devices, associated with a user, such as personal computers, tablets, smartphones, and the like.

In the context of the present specification, the expression "computer readable storage medium" (also referred to as "storage medium" and "storage") is intended to include non-transitory media of any nature and kind whatsoever, including without limitation RAM, ROM, disks (CD-ROMs, DVDs, floppy disks, hard drivers, etc.), USB keys, solid state-drives, tape drives, etc. A plurality of components may be combined to form the computer information storage media, including two or more media components of a same type and/or two or more media components of different types.

In the context of the present specification, a "database" is any structured collection of data, irrespective of its particular structure, the database management software, or the computer hardware on which the data is stored, implemented or otherwise rendered available for use. A database may reside on the same hardware as the process that stores or makes use of the information stored in the database or it may reside on separate hardware, such as a dedicated server or plurality of servers.

In the context of the present specification, the expression "information" includes information of any nature or kind whatsoever capable of being stored in a database. Thus, information includes, but is not limited to audiovisual works (images, movies, sound records, presentations etc.), data (location data, numerical data, etc.), text (opinions, comments, questions, messages, etc.), documents, spreadsheets, lists of words, etc.

In the context of the present specification, the expression "communication network" is intended to include a telecommunications network such as a computer network, the Internet, a telephone network, a Telex network, a TCP/IP data network (e.g., a WAN network, a LAN network, etc.), and the like. The term "communication network" includes a wired network or direct-wired connection, and wireless media such as acoustic, radio frequency (RF), infrared and other wireless media, as well as combinations of any of the above.

In the context of the present specification, the term "application" refers to a software present on an electronic device and provided with a user interface. The application can rely on processing means to process data and issue information. The application may also communicate over a communication network with a database.

In the context of the present specification, the words "first", "second", "third", etc. have been used as adjectives only for the purpose of allowing for distinction between the nouns that they modify from one another, and not for the purpose of describing any particular relationship between those nouns. Thus, for example, it should be understood that, the use of the terms "server" and "third server" is not intended to imply any particular order, type, chronology, hierarchy or ranking (for example) of/between the server, nor is their use (by itself) intended imply that any "second server" must necessarily exist in any given situation. Further, as is discussed herein in other contexts, reference to a "first" element and a "second" element does not preclude the two elements from being the same actual real-world element. Thus, for example, in some instances, a "first" server and a "second" server may be the same software and/or hardware, in other cases they may be different software and/or hardware.

In the context of the present specification, the word "about" when used in relation to numerical designations or ranges means the exact numbers plus or minus experimental measurement errors and plus or minus 10 percent of the exact numbers.

Moreover, all statements herein reciting principles, aspects, and implementations of the present technology, as well as specific examples thereof, are intended to encompass both structural and functional equivalents thereof, whether they are currently known or developed in the future. Thus, for example, it will be appreciated by those skilled in the art that any block diagrams or illustrations represent conceptual views of the principles of the present technology. Similarly, it will be appreciated that any diagrams, flowcharts, and the like represent various processes which may be substantially represented in computer-readable media and so executed by a computer or processor, whether or not such computer or processor is explicitly shown.

Implementations of the present technology each have at least one of the above-mentioned object and/or aspects, but do not necessarily have all of them. It should be understood that some aspects of the present technology that have resulted from attempting to attain the above-mentioned object may not satisfy this object and/or may satisfy other objects not specifically recited herein.

Additional and/or alternative features, aspects and advantages of implementations of the present technology will become apparent from the following description, the accompanying drawings and the appended claims.

The present invention is based on the holistic collection of a number of useful biomarkers which are analyzed and depicted in a form of an individual biomarker profile otherwise known as a digital twin profile. This digital twin can be used to generate a phenotype profiling. This refers to providing as many biomarker readings and analysis as possible to generate a phenotype digital twin.

The number of biomarkers that are featured in a digital twin profile can vary, for example from about 10 to about 100 to about 1000 or more depending on the level of detail required. A fully phenotyped digital twin may not be necessary before drawing useful information from the present invention.

The digital twin profile can be rebuilt at various time intervals to track variations over time. These variations can result for example from disease progression, lifestyle or training changes, aging, nutrition modifications, weight variations, exercise and/or medications.

Instead of focusing on individual biomarkers and making predictions or recommendations based on the biomarker measurement(s), the present invention is directed to the establishment and tracking of a digital twin profile of a holistic combination of biomarkers. Thus, in one embodiment, the present invention provides a system for measuring and creating a digital twin profile providing a phenotyped digital twin.

Figure 3:
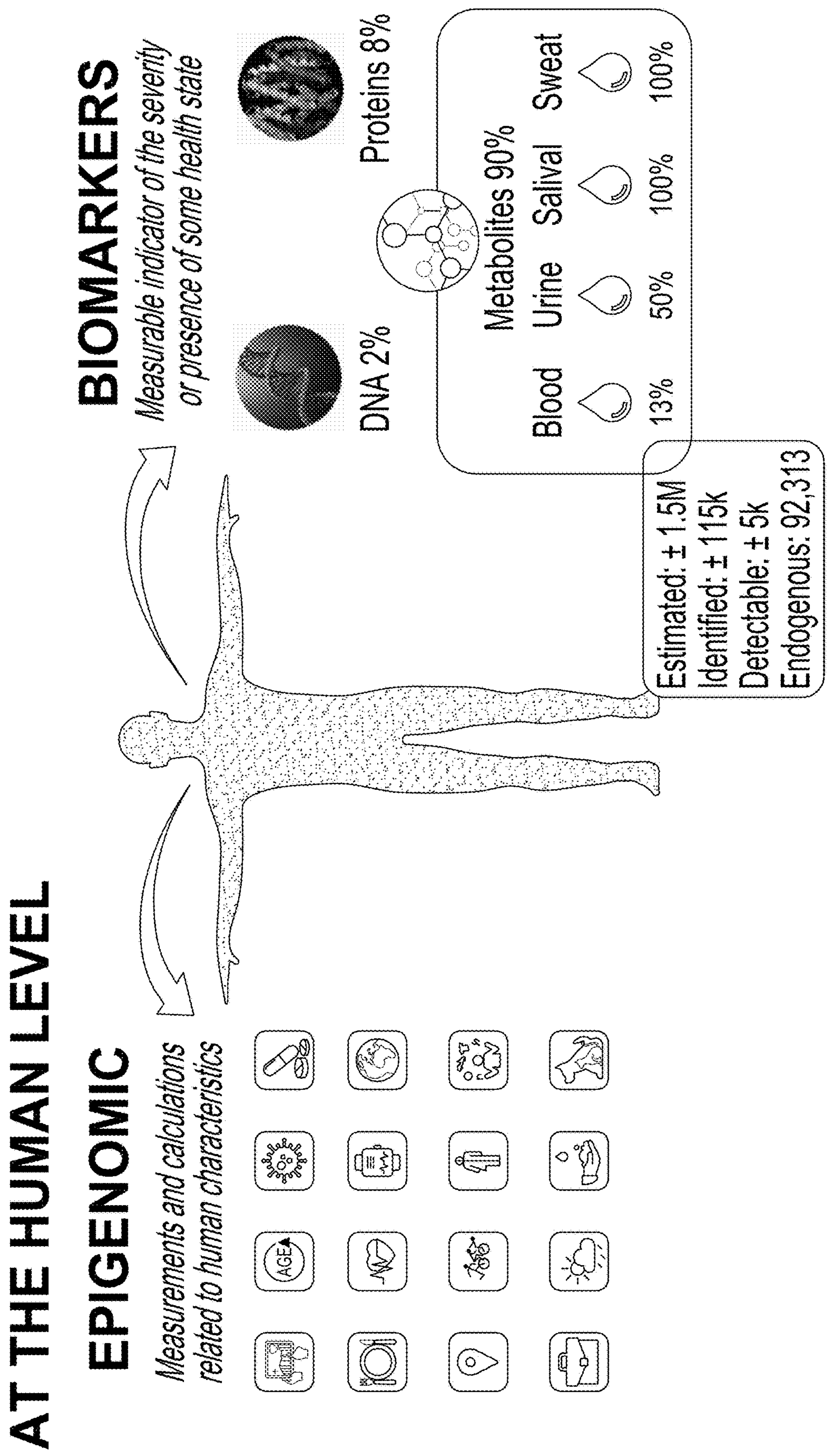
FIG. 3 is an illustration of the sources of biomarkers and their counterpart measurements.

Referring to FIG. 1, in embodiments of the present invention, the service is provided for sports training, therapy, rehabilitation, wellness or medical professionals. Clients or patients receive a testing kit for self-collection of biofluid, tissue or microbiome samples (from home). The testing kit can be provided by a professional or ordered from a third party and delivered to the client or patient. As illustrated in FIG. 3, many biofluid samples can be collected, such as blood, saliva, tears, sweat, vaginal cultures, semen or urine. Tissue samples can include for example hair, follicles, nails, shed skin or tissues obtained by biopsy. Microbiome samples can for example be stool samples. Sample collection is performed at home by the patient/client himself or can alternatively, occur at a designated location providing professional assistance.

In practice, samples are returned by mail to a laboratory for testing of biomarkers. Apart from comparing the biomarker readings to preferred and predetermined ranges, all biomarkers are added to a consortium of data and results that forms a digital twin of the individual client or patient.

Figure 2:
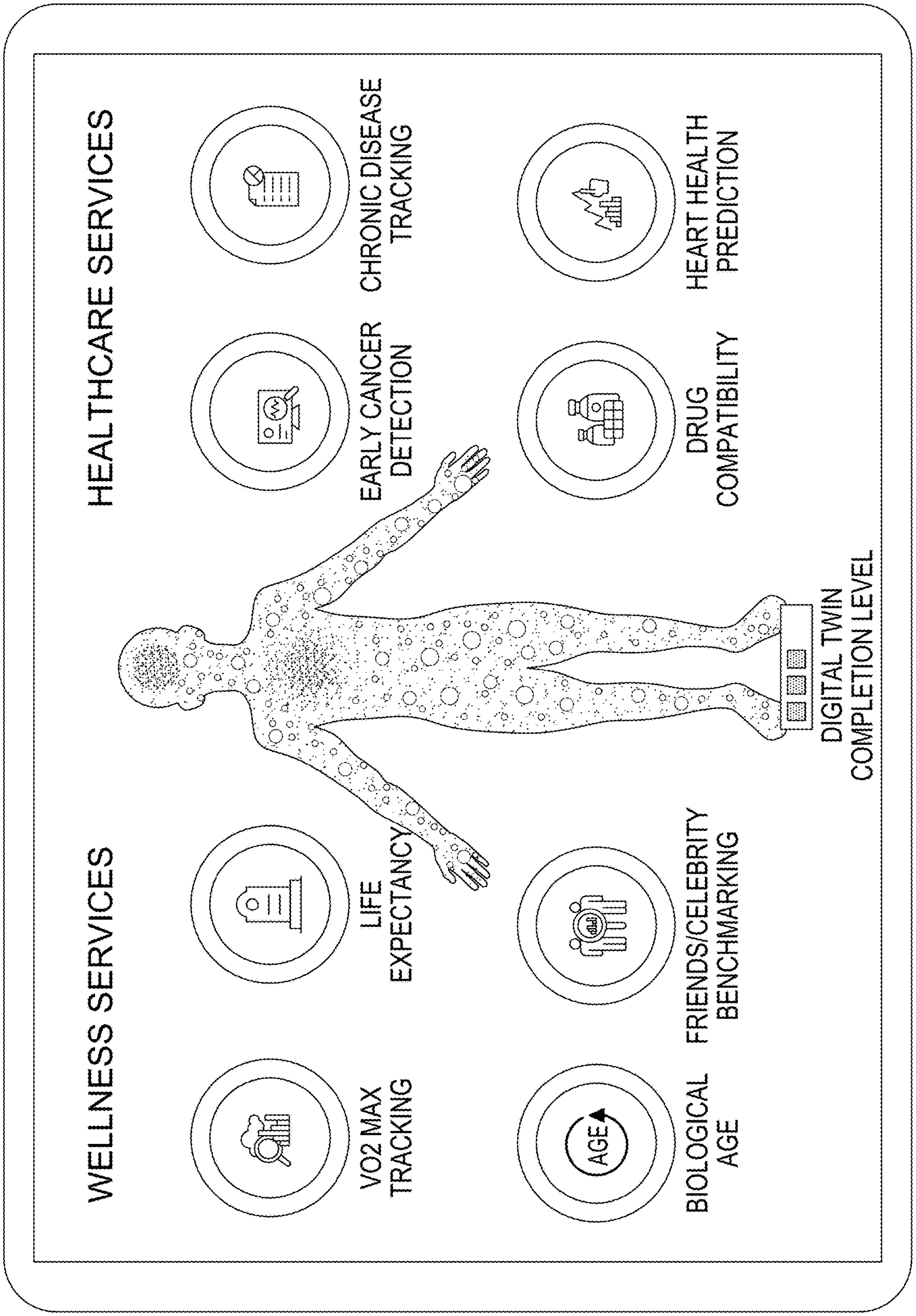
FIG. 2 is an illustration of a graphical output of a client/patient application screen in accordance with one particular embodiment of the invention.

In preferred embodiments, a sufficiently large number of biomarkers are measured and recorded to provide a suitable basis for accurate phenotyping of the digital twin. Referring to FIG. 2, incomplete phenotyping can be illustrated by a bar graph or otherwise to signal to the client/patient or professional assisting the client/patient that the phenotyping is yet to be completed.

In preferred embodiments, the phenotyping is provided by graphical representation such as bar graph plotting all biomarkers (not shown). This graph, in some embodiments a bar graph or histogram, provides a unique biomarker phenotyping of the individual client or patient, akin to a fingerprint.

This technique can be repeated over time at some intervals such as, for example, every three or six months so as to provide a shifting of the shape of the biomarker phenotyping in response to individual recommendations, such as nutrition, diet, sleep, exercise, training, rest, and other lifestyle or medication recommended by the laboratory or the professional that follows the client or patient.

Referring again to FIG. 1, in preferred embodiments, artificial intelligence, including machine learning are used to compare known outcomes and predictions to individual biomarker phenotyping essentially by comparing the graphical shape of the biomarker phenotyping or by statistical analysis. Comparing the graphical shape of the biomarker phenotyping is akin to fingerprint comparisons with software to find matches and correlations. The modifications over time of the biomarker phenotyping can also be used to predict outcomes and predispositions towards specific or general health parameters or conversely towards disease apparition or progression. These modifications can also be used to run simulations based on trend analysis and artificial intelligence where a databased and machine learning algorithms (MLAs) are used for predictions and simulations.

Figure 4:
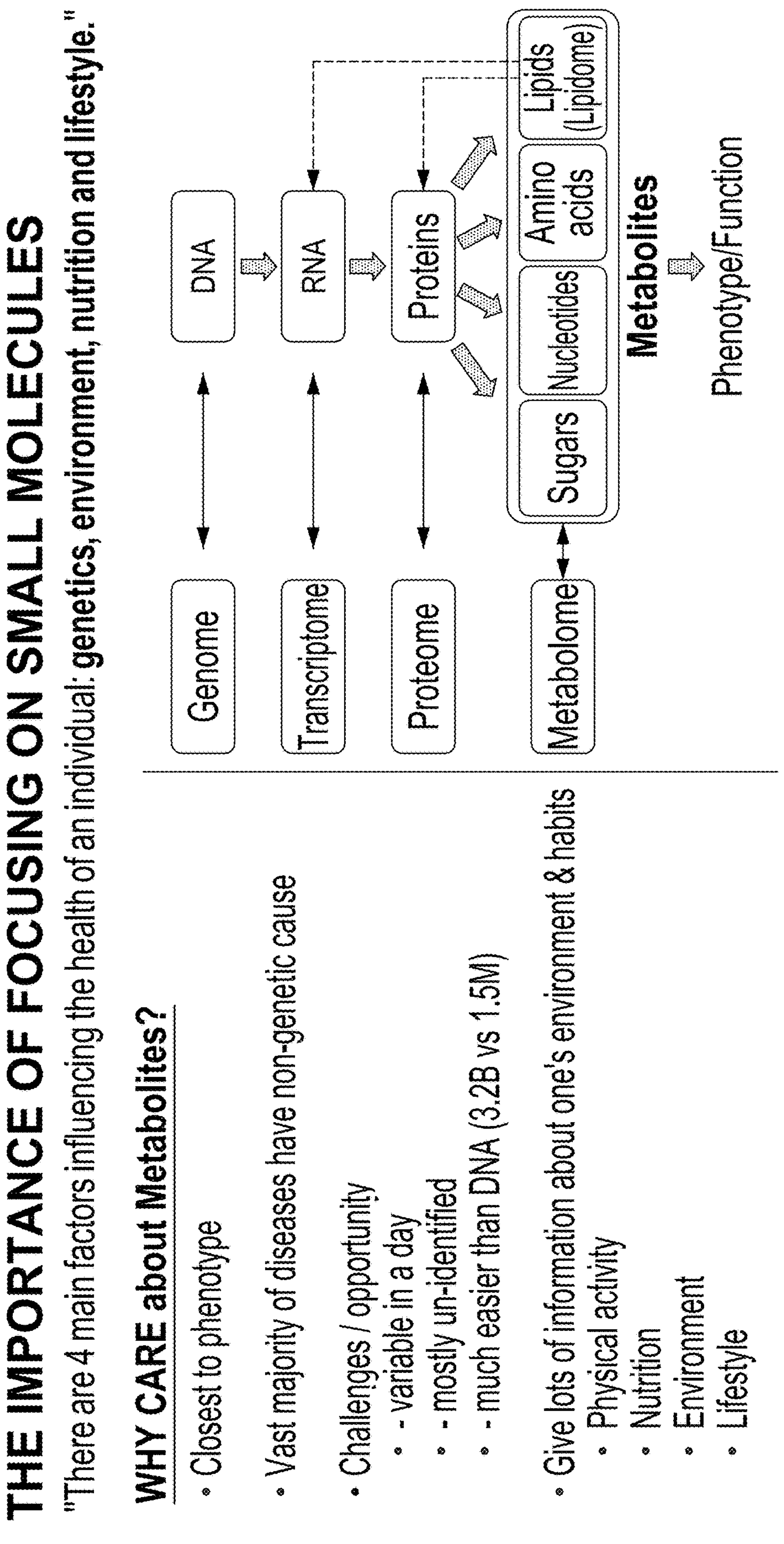
FIG. 4 is an illustration of the importance of metabolites in a digital twin phenotyping.

In embodiments, as illustrated in FIG. 4, the previously described system can be used by sports trainers, therapists, rehabilitation or wellness professionals to predict and improve various factors such as whole health index, biological age and life expectancy measurements, body composition analysis, energy balance, performance, libido, drive, stress management, sleep quality and quantity overtraining, aerobic capacity and benchmarking of these in comparison to known celebrities, friends, training partners or others.

In embodiments, the above described system can be used by medical professionals to predict and improve various factors such as disease risks and factors such as heart health, heart disease, cardiovascular disease, stroke, hemorrhage, mental disease, cancer, chronic diseases or conditions such as chronic pain, fibromyalgia, autoimmune diseases such as lupus, asthma, eczema, psoriasis, Crohn's, colitis, diverticulitis, constipation, diarrhea, allergies, intolerances, Parkinson disease, Alzheimer, dementia, drug treatment compatibility, dietary needs, exercise or lifestyle requirements, injury, inflammation, infection, virus load, antibodies and vaccine requirements.

In practice, the system of the present invention empowers sports trainers, therapists, rehabilitation, wellness and medical experts to provide more informed and personalized precision interventions for their clients and patients. These experts can include for example, sports therapists, physiotherapists, chiropractors, osteopaths and related professionals. By tracking the biomarker phenotyping over time, professionals can consider and appraise the effect of recommendations, treatments and simulations of treatments by being proactive rather than reactive.

In one or more embodiments of the phenotyping system, collected biomarker data is entered in a network having access to a processor having access to a set of machine learning algorithms (MLAs) having been trained to determine the optimal health and wellness parameters at the time of processing or over time and based on the age and other parameters of the client/patient.

In one or more embodiments, the set of machine learning algorithms (MLAs) has been trained to provide predictions and simulations of health and biomarker outcomes over time. The set of MLAs is also used to provide recommendations to various aspects of the client/patient nutrition, exercise, rest, sleep, relaxation, medication or fluid intake so as to provide improved outcomes in terms of biomarkers and other sports performance such as $VO_2$Max, wellness and health parameters.

In embodiments, the system of the present invention provides a database and MLAs for storing biomarker data and a comparative knowledge base of biomarker and performance, wellness and health parameters over a large number of subjects and a comparative knowledge base on predictors and diseases or conditions. The database is constantly improved upon by the MLAs so as to become more accurate. In embodiments, the ensemble of biomarker data collected for a specific client/patient provides a digital twin phenotyping or phenotype. This digital twin is compared to the knowledge bases to provide an assessment, over time, of the client/patient. The assessment is done by graphical comparison or statistical data analysis of the digital twin in comparison with known phenotypes and diseases or conditions. One or more processor is used in conjunction with the database to provide data outputs and results and to run simulations or outcome predictions such as probable disease progression. The processor also provides recommended changes to various controllable parameters such as nutrition, treatments, medications, sleep, rest, fluid intake, training, exercise and types, duration, intensity levels of training and exercise. These recommended changes are designed to improve performance, health and wellness outcomes, over time, for the client/patient.

The database is accessible via a network and via electronic communication means.

In embodiments, the system of the present invention also provides a software product such as a smartphone application providing data, results, predictions, simulations and guidance. In a preferred embodiment, the application provides a client/patient module with content and functionalities for the client/patient and a second related application for the professional.

Referring again to FIG. 2, the client/patient version of the application provides functionalities, data and results on features of the digital twin and recommended dietary needs, exercise or lifestyle requirements, injury treatment, and vaccine or other requirements. The application also provides tracking of data over time and comparison with preferred data values or comparisons with known celebrities, friends, training partners or others, as benchmarks. The application also provides basic simulation functions showing how data changes can affect the overall digital twin and lead to improved outcomes for the client/patient.

The professional version of the application provides extended functionalities, prediction and simulation functions and recommended treatments or regimens or general advice. For example, the extended simulation functions allows the professional to canvass various scenarios and better understand the effect and leverage of various biomarkers on real world outcomes. These functionalities allow the professional to provide precise interventions with their client/patients.

Figure 5:
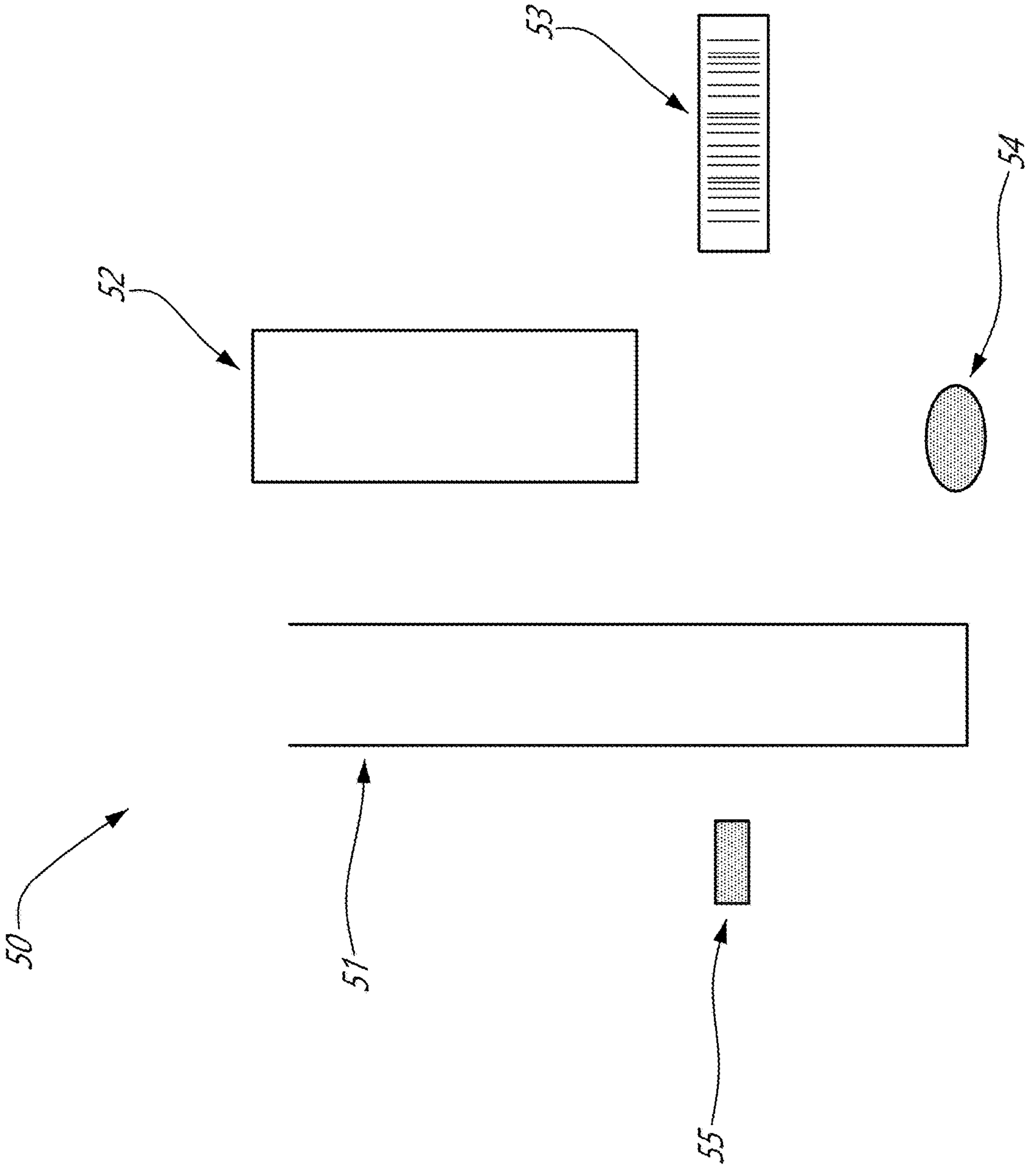
FIG. 5 is an illustration of a sampling kit in one embodiment.

Also provided, and illustrated in FIG. 5, is a sampling kit 50 for implementing step a) in accordance with claim 1, the sampling kit 50 comprising a fluid sample collection device 51 and instructions for use 52, said sampling kit 50 comprising a code such as a barcode 53 for identification of the subject providing said sample, said sampling kit 50 further providing a stabilizer 54 to stabilize said sample during shipment, said sampling kit 50 further providing anti-tampering features 55 such as chemical inactivation of the sample if kit tampering occurs.

Those skilled in the art will recognize, or be able to ascertain, using no more than routine experimentation, numerous equivalents to the specific procedures, embodiments, claims, and examples described herein. Such equivalents are considered to be within the scope of this invention and covered by the claims appended hereto.

What is claimed is:

1. A method of using digital twin biomarker profiles for providing recommendations to a user for improved sporting, therapy, wellness and healthcare outcomes, the method comprising:

a) sampling a plurality of biomarkers from a subject using a sampling kit to collect at least one sample from the subject, the sampling kit comprising a fluid sample collection device and instructions for use, the sampling kit comprising an identification of the subject, the sampling kit further providing anti-tampering features;

b) receiving and analyzing the plurality of biomarkers previously obtained via the sampling kit to output, by way of a processor and a machine learning algorithm (MLA), a digital twin phenotype profile;

c) comparing, by way of the processor and the MLA, either graphically or statistically the digital twin phenotype profile to one or more knowledge bases collectively including biomarker data from the subject, at least one other subject, or a combination thereof and including data on diseases, conditions, and predictors of those diseases and conditions to find matches and correlations between the digital twin phenotype profile and the data in the one or more knowledge bases;

d) generating, by way of the processor and the MLA, a set of recommended changes on controllable parameters of the subject, the controllable parameters comprising: dietary, exercise, and lifestyle requirements; and e) generating, by way of the processor and the MLA, simulations or outcome predictions based on the results of the comparison of the digital twin phenotype profile to the knowledge base, the set of recommended changes generated, or a combination thereof, the simulations or outcome predictions showing the overall effect of data changes on the digital twin phenotype profile and improved outcomes for the subject.

2. The method of claim 1 wherein the biomarkers number at least 10.

3. The method of claim 1 wherein the biomarkers number at least 100.

4. The method of claim 1 wherein the biomarkers number at least 200.

5. The method of claim 1 wherein the biomarkers are indicative of parameters useful to benchmark sports performance or sports therapy or other forms of therapy.

6. The method of claim 1 wherein the biomarkers are indicative of wellness parameters, the wellness parameters comprising: overall health, sleep, nutrition, life expectancy, biological age, energy levels, body mass index, flexibility, and strength.

7. The method of claim 1 wherein the biomarkers are indicative of health or disease results or parameters or progression thereof.

8. The method of claim 7 wherein the biomarkers number at least 10.

9. The method of claim 7 wherein the biomarkers number at least 100.

10. The method of claim 7 wherein the biomarkers number at least 200.

11. The method of claim 1 wherein the biomarkers consist of measurements from tissue or fluid samples.

12. The method of claim 11 wherein the tissue or fluid samples comprise at least one of: blood, saliva, tears, sweat, vaginal cultures, semen, or urine.

13. The method of claim 1 wherein the biomarkers comprise at least one level of: minerals, hormones, proteins, fats, sugars, vitamins, metabolites, microbiomes, analytes, enzymes, antigens, or antibodies.

14. The method of claim 1 wherein the anti-tampering features of the sampling kit include chemically inactivating the sample if kit tampering occurs.

15. The method of claim 1 wherein the digital twin phenotype profile outputting and the comparison of the digital twin phenotype profile to the knowledge base are repeated when receiving at least one new biomarker.

16. The method of claim 1 further comprising storing the digital twin phenotype profile in a database with the knowledge base.

17. The method of claim 1 further comprising:

adjusting the set of recommended changes; and generating, by way of the processor and the MLA, simulations or outcome predictions based on the adjusted set of recommended changes.

18. The method of claim 1 wherein generating the simulations or outcome predictions comprises generating a probable disease progression.

* * * * *